United States Patent
Sakamoto et al.

(10) Patent No.: US 6,300,513 B2
(45) Date of Patent: Oct. 9, 2001

(54) METHOD OF STABILIZING N-OXYL COMPOUNDS IN VINYL COMPOUNDS

(75) Inventors: Kazuhiko Sakamoto; Naoki Serata; Kouji Ueno; Sei Nakahara; Masatoshi Ueoka, all of Himeji (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/729,760

(22) Filed: Dec. 5, 2000

(30) Foreign Application Priority Data

Dec. 24, 1999 (JP) .................................................. 11-368430

(51) Int. Cl.[7] .......................... C07C 69/54; C07C 57/075

(52) U.S. Cl. ................................ 560/4; 562/598; 546/184

(58) Field of Search .................................. 560/4; 562/598

(56) References Cited

U.S. PATENT DOCUMENTS

| 5,322,960 | 6/1994 | Sakamoto et al. ................... 560/205 |
| 5,504,243 | * 4/1996 | Sakamoto et al. ................... 560/205 |

FOREIGN PATENT DOCUMENTS

| 40-14121 | 3/1992 | (JP) ................................. C08F/2/38 |

* cited by examiner

*Primary Examiner*—Bernard Dentz
(74) *Attorney, Agent, or Firm*—Mathews, Collins, Shepherd & Gould, P.A.

(57) ABSTRACT

It intends to prevent the reduction in quantity with time of an oxyl compound in vinyl compounds. The quantity reduction of the N-oxyl compound is suppressed by causing an N-oxyl compound, N-hydroxy-2,2,6,6-tetramethylpiperidine compound and a 2,2,6,6-tetramethylpiperidine compound to co-exist in vinyl compounds.

12 Claims, No Drawings

METHOD OF STABILIZING N-OXYL COMPOUNDS IN VINYL COMPOUNDS

BACKGROUND OF THE INVENTION

1. Field of the Invention

The present invention relates to a method of stabilizing N-oxyl compounds in vinyl compounds.

2. Description of the Related Art

It is well known that vinyl compounds such as (meth) acrylic acid and esters thereof are liable to polymerize by light and heat. In order to prevent polymerization of vinyl compounds, various kinds of polymerization inhibitors are added therein.

JP-B-4-14121 describes to use N-oxyl compounds such as bis-(2,2,6,6-tetramethyl-4-piperidinoxyl)-sebacate as a polymerization inhibitor for vinyl compounds.

SUMMARY OF THE INVENTION

We have researched stability of the vinyl compounds in which N-oxyl compounds have been added as a polymerization inhibitor during storage or transportation thereof, and then found the following: Such N-oxyl compounds were lost with time in the vinyl compounds, so that the vinyl compounds could not be stably stored or transported.

With a view to the above circumstance, it is an object of the present invention to provide a method of stabilizing N-oxyl compounds in vinyl compounds.

We have found that by allowing an N-oxyl compound in vinyl compounds to co-exist with an N-hydroxy-2,2,6,6-tetramethylpiperidine compound and a 2,2,6,6-tetramethylpiperidine compound, a disappearance of the N-oxyl compound with time can be reduced, and then the present invention has been achieved.

According to the present invention, there is provided a method of stabilizing an N-oxyl compound in vinyl compounds by allowing the N-oxyl compound in the vinyl compounds to co-exist with an N-hydroxy-2,2,6,6-tetramethylpiperidine compound and a 2,2,6,6-tetramethylpiperidine compound.

In accordance with the present invention, the reduction in concentration of the N-oxyl compound that has been added in the vinyl compounds for a stabilizer is controlled, and then the vinyl compound is maintained stably. More specifically, in accordance with the present invention, the concentration reduction of N-oxyl compounds in the vinyl compound can be controlled and then the vinyl compound can be stably maintained in the case of handling the vinyl compound, such as storing in a tank, transportation by a tank truck and piping.

The above and other objects, features and advantages of the present invention will become clear from the following description of the preferred embodiments.

DESCRIPTION OF THE PREFERRED EMBODIMENTS

The viny compound to be used in the present invention is a compound having a vinyl bond and polymerizable during the production or handling thereof, and may include for example (meth)acrylic acid, esters thereof and acrylonitrile. Among them, (meth)acrylic acid and esters thereof are more preferable.

As the representative of acrylic esters, it may cite methyl acrylate, ethyl acrylate, butyl acrylate, 2-hydroxyethyl acrylate and 2-hydroxypropyl acrylate, etc. As the representative of methacrylic esters, it may cite methyl methacrylate, butyl methacrylate, 2-hydroxyethyl methacrylate and 2-hydroxypropyl methacrylate, etc.

The amount of N-oxyl compounds to be used is not particularly restricted as long as polymerization of vinyl compounds can be prevented, but may be in the range of 0.0005 to 0.1 part by weight, based on 100 parts by weight of the vinyl compound.

The N-oxyl compound to be used in the present invention is not particularly restricted, but may include N-oxyl compounds, which are generally used for preventing polymerization of the vinyl compounds. Among them, 2,2,6,6-tetramethylpiperidinoxyl compounds represented by the formula (1):

(1)

$$\begin{array}{c} R^2 \diagdown \diagup R^1 \\ H_3C \diagdown \diagup CH_3 \\ H_3C \diagdown N \diagup CH_3 \\ | \\ O \cdot \end{array}$$

wherein $R^1$ stands for CHOH, CHCH$_2$OH, CHCH$_2$CH$_2$OH, CHOCH$_2$OH, CHOCH$_2$CH$_2$OH, CHCOOH or C=O, and $R^2$ stands for a hydrogen atom or CH$_2$OH, are preferable.

As the representative of 2,2,6,6-tetramethylpiperidinoxyl compounds, 4-hydroxy-2,2,6,6-tetramethylpiperidinoxyl, 4-oxo-2,2,6,6-tetramethylpiperidinoxyl, and 4-carboxy-2,2,6,6-tetramethylpiperidinoxyl, etc may be cited. The N-oxyl compound may be used singly or in a combination of two or more thereof. Among them, 4-hydroxy-2,2,6,6-tetramethylpiperidinoxyl and 4-oxo-2,2,6,6-tetramethylpiperidinoxyl are preferable, and 4-hydroxy-2,2,6,6-tetramethylpiperidinoxyl is most preferable.

As the representative of N-hydroxy-2,2,6,6-tetramethylpiperadine compounds, 1,4-dihydroxy-2,2,6,6-tetramethylpiperidine, and 1-hydroxy-2,2,6,6-tetramethylpiperidine, etc may be cited. The N-hydroxy-2,2,6,6-tetramethylpiperidine compounds may be used singly or in a combination of two or more thereof.

The amount of the N-hydroxy-2,2,6,6-tetramethylpiperidine compound is not particularly restricted as long as reduction in the amount of the N-oxyl compound with time can be controlled, but may be in the range of 0.01 to 500 parts by weight, preferably 0.1 to 150 parts by weight, based on 100 parts by weight of the N-oxyl compound.

As the representative of 2,2,6, 6-tetramethylpiperidine compounds, 2,2,6,6-tetramethylpiperidine, and 4-hydroxy-2,2,6,6-tetramethylpiperidine, etc may be cited. The 2,2,6, 6-tetramethylpiperidine compounds may be used singly or in a combination of two or more thereof.

The amount of the 2,2,6,6-tetramethylpiperidine compound is not particularly restricted as long as reduction in the amount of the N-oxyl compound with time can be controlled, but may be in the range of 0.01 to 500 parts by weight, preferably 0.1 to 150 parts by weight, based on 100 parts by weight of the N-oxyl compound.

A method of adding to the vinyl compounds, the N-oxyl compound, the N-hydroxy-2,2,6,6-tetramethylpiperidine compound and the 2,2,6,6-tetramethylpiperidine compound is not particularly restricted, and they may be added separately or simultaneously.

The vinyl compound to be used in the present invention may include impurities which were by-produced in the production thereof, or derived from the raw materials therefor. When acrylic acid is used for the vinyl compound, an advantageous stabilizing effect of the present invention can be expected even if water, organic acids such as acetic acid, aldehydes such as acrolein and the like are contained.

In the present invention, conventional polymerization inhibitors such as phenothiazine, methoquinone, copper dialkyldithiocarbamate, manganese acetate, p-phenylenediamine or the like may be additionally incorporated in the vinyl compounds. The amount of the conventional polymerization inhibitors is not particularly restricted as long as it may be usually used, but may be in the range of 0.0005 to 0.1 part by weight, based on 100 parts by weight of the vinyl compound.

In accordance with the present invention, the quantity reduction of the N-oxyl compounds in the vinyl compound can be effectively controlled or suppressed in the case of handling the vinyl compounds, such as storing in a tank, transportation by a tank track, and piping. As a result, polymerization of the vinyl compounds can be also prevented.

EXAMPLES

The following examples are described several preferred embodiments to illustrate the invention. However, it is to be understood that the invention is not intended to be limited to the specific embodiments.

The amounts of 4-hydroxy-2,2,6,6-tetramethylpiperidinoxyl (referred to as "4H-TEMPO"), 1,4-dihydroxy-2,2,6,6-tetramethylpiperidine (referred to as "1,4DH-TEMP"), and 4-hydroxy-2,2,6,6-tetramethylpiperidine (referred to as "4H-TEMP") are measured by a liquid chromatography.

Examples

Samples of acrylic acid solutions were prepared by dissolving a stabilizer having a composition and concentration shown in the following Table 1 in acrylic acid which polymerization inhibitors had been removed by distillation, respectively in each sample tubes. The samples were preserved at room temperature (25° C.). Each samples was measured for the concentration of 4H-TEMPO in acrylic acid from 30 minutes to 10 hours after the dissolution. These results obtained are shown in Table 2 below.

TABLE 1

| | Concentration of the stabilizer (ppm) | | |
|---|---|---|---|
| | 4H-TEMPO | 1,4DH-TEMP | 4H-TEMP |
| 1(Ex) | 100 | 100 | 100 |
| 2(Ex) | 96 | 2 | 2 |
| 3(C-Ex) | 100 | 200 | — |
| 4(C-Ex) | 100 | — | 200 |
| 5(C-Ex) | 100 | — | — |

(Ex): Example (C-Ex): Comparative Example

TABLE 2

| | Concentration of 4H-TEMPO (ppm) | | | |
|---|---|---|---|---|
| | 30 min. later | 2 hrs. later | 5 hrs. later | 10 hrs. later |
| 1(Ex) | 100 | 100 | 100 | 98 |
| 2(Ex) | 92 | 77 | 70 | 65 |
| 3(C-Ex) | 62 | 45 | 32 | 21 |

TABLE 2-continued

| | Concentration of 4H-TEMPO (ppm) | | | |
|---|---|---|---|---|
| | 30 min. later | 2 hrs. later | 5 hrs. later | 10 hrs. later |
| 4(C-Ex) | 58 | 43 | 30 | 18 |
| 5(C-Ex) | 49 | 31 | 22 | 13 |

(Ex): Example (C-Ex): Comparative Example

It is clear from the above Tables that the prevention of the reduction of 4H-TEMPO, i.e. an N-oxyl compound which is used as the stabilizer for vinyl compounds in the present invention are found compared to the comparative examples.

The entire disclosure of Japanese Patent Application No. 11-368430 filed on Dec. 24, 1999 including specification, claims and summary are incorporated herein by reference in its entirety.

What is claimed is:

1. A method of stabilizing an N-oxyl compound in vinyl compounds, which comprises causing the N-oxyl compound, an N-hydroxy-2,2,6,6-tetramethylpiperidine compound and a 2,2,6,6-tetramethylpiperidine compound to co-exist in the vinyl compound.

2. A method according to claim 1, wherein the vinyl compound is (meth)acrylic acid or esters thereof.

3. A method according to claim 1, wherein the amount of the N-hydroxy-2,2,6,6-tetramethylpiperidine compound is in the range of 0.01 to 500 parts by weight, and the amount of the 2,2,6,6-tetramethylpiperidine compound is in the range of 0.01 to 500 parts by weight, based on 100 parts by weight of the N-oxyl compound, respectively.

4. A method according to claim 2, wherein the amount of the N-hydroxy-2,2,6,6-tetramethylpiperidine compound is in the range of 0.01 to 500 parts by weight, and the amount of the 2,2,6,6-tetramethylpiperidine compound is in the range of 0.01 to 500 parts by weight, based on 100 parts by weight of the N-oxyl compound, respectively.

5. A method according to claim 1, wherein the N-oxyl compound is 4-hydroxy-2,2,6,6-tetramethylpiperidinoxyl, the N-hydroxy-2,2,6,6-tetramethylpiperidine compound is 1,4-dihydroxy-2,2,6,6-tetramethylpiperidine, and the 2,2,6,6-tetramethylpiperidine compound is 4-hydroxy-2,2,6,6,-tetramethylpiperidine.

6. A method according to claim 4, wherein the N-oxyl compound is 4-hydroxy-2,2,6,6-tetramethylpiperidinoxyl, the N-hydroxy-2,2,6,6-tetramethylpiperidine compound is 1,4-dihydroxy-2,2,6,6-tetramethylpiperidine, and the 2,2,6,6-tetramethylpiperidine compound is 4-hydroxy-2,2,6,6,-tetramethylpiperidine.

7. A method according to claim 1, wherein the amount of the N-oxyl compound is in the range of 0.0005 to 0.1 part by weight based on 100 parts by weight of the vinyl compound.

8. A method according to claim 6, wherein the amount of the N-oxyl compound is in the range of 0.0005 to 0.1 part by weight based on 100 parts by weight of the vinyl compound.

9. A method according to claim 1, wherein the stabilizing is effected for storing, transporting by a tank truck or piping the vinyl compounds.

10. A method according to claim 8, wherein the stabilizing is effected for storing, transporting by a tank truck or piping the vinyl compounds.

11. A method according to claim 1, wherein the amount of the N-hydroxy-2,2,6,6-tetramethylpiperidine compound is in the range of 0.1 to 150 parts by weight, and the amount of the 2,2,6,6-tetramethylpiperidine compound is in the range of 0.1 to 150 parts by weight, based on 100 parts by weight of the N-oxyl compound, respectively.

12. A method according to claim 10, wherein the amount of the N-hydroxy-2,2,6,6-tetramethylpiperidine compound is in the range of 0.1 to 150 parts by weight, and the amount of the 2,2,6,6-tetramethylpiperidine compound is in the range of 0.1 to 150 parts by weight, based on 100 parts by weight of the N-oxyl compound, respectively.

* * * * *